(12) United States Patent
Raman

(10) Patent No.: US 6,309,626 B1
(45) Date of Patent: Oct. 30, 2001

(54) SUNSCREEN COMPOSITION

(75) Inventor: Govindarajan Raman, Karnataka (IN)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/425,718

(22) Filed: Oct. 22, 1999

(30) Foreign Application Priority Data

Oct. 23, 1998 (IN) .............................................. 678/BOM/98
Dec. 16, 1998 (GB) .................................................. 9827703

(51) Int. Cl.⁷ ................................ A61K 7/42; A61K 7/00
(52) U.S. Cl. .............................................. 424/59; 424/401
(58) Field of Search ........................................ 424/401, 59

(56) References Cited

U.S. PATENT DOCUMENTS

| | | | |
|---|---|---|---|
| 4,562,067 | 12/1985 | Hopp et al. | 424/59 |
| 4,724,137 | 2/1988 | Hoppe et al. | 424/59 |
| 4,797,272 * | 1/1989 | Linn et al. | 424/59 |
| 4,840,788 * | 6/1989 | Beachell | 424/59 |
| 6,077,520 * | 6/2000 | Tominaga | 424/401 |

FOREIGN PATENT DOCUMENTS

| | | |
|---|---|---|
| 0 013 390 | 7/1980 | (EP) . |
| 0 044 976 | 2/1982 | (EP) . |
| 0 046 723 | 3/1982 | (EP) . |
| 0 153 089 | 8/1985 | (EP) . |
| 0 166 221 | 1/1986 | (EP) . |
| 0 396 422 | 11/1990 | (EP) . |
| 1 370 236 | 10/1974 | (GB) . |
| 83/02941 | 9/1983 | (WO) . |

* cited by examiner

Primary Examiner—Jose' G. Dees
Assistant Examiner—Kato M. George
(74) Attorney, Agent, or Firm—Milton L. Honig

(57) ABSTRACT

A process for preparing a sunscreen composition is provided which includes the steps of (i) dissolving an ultraviolet radiation absorbing sunscreen in an oil phase; (ii) neutralizing stearic acid in a water phase; and (iii) homogenising the dissolved sunscreen with the neutralised stearic acid in a cosmetically acceptable vehicle.

5 Claims, No Drawings

SUNSCREEN COMPOSITION

TECHNICAL FIELD OF THE INVENTION

The present invention relates to an improved cosmetic sunscreen composition for topical application to human skin to provide enhanced protection from sunlight and a process for preparing the same.

BACKGROUND AND PRIOR ART

Melanin is the black pigment synthesised by the action of the enzyme tyrosinase on the amino acid tyrosine. The reaction takes place in organelles called melanosomes contained within cells called melanocytes. Melanocytes transfer melanosomes with melanin to neighbouring keratinocytes which harbour these organelles till they are themselves shed from the body from the superficial layers of the skin. The intensity of the skin colour is directly related to the number, the size, melanin content, the rate of formation and transfer of melanosomes to keratinocytes. Melanin is also an important protectant of skin and tissues beneath the skin as it has the capacity to absorb incident ultraviolet light.

The UV range is divided into three regions, UV-A, having a wavelength of from about 320 to 400 nm which gives a tanning effect without inflammation; UV-B, having a wavelength of from about 290–320 nm which is responsible for erythema (sunburn) and eventually for tanning; and UV-C, having a wavelength of from about 200–290 nm, normally absorbed by the ozone layer in the earth's atmosphere, but which is potentially very damaging to the skin.

Melanogenesis and pigmentation of the skin are closely related responses to irradiation by UV light. The photobiological changes that cause erythema also lead to melanogenesis and increased pigmentation. Hence exposure to sunlight leads to darkening of the skin by immediate pigment darkening of already formed melanin, and also by formation of new melanin. Many skin compositions are formulated for the purpose of maintaining the colour of the skin against darkening following exposure to ultra-violet light. These compositions have been based on materials which deflect and scatter incident ultra-violet light of the wavelength which produce burning and tanning of the skin or which absorb this light.

To prevent darkening of existing melanin and formation of new melanin, the skin has to be protected broadly across the Uv-A range of from about 320–400 nm. We have found that by careful selection of sunscreens we can protect the skin against the darkening effects of radiation.

GB 1 370 236 discloses a skin lightening composition containing niacin and the method by which it effects skin lightening is by retardation of melanin dispersion or distribution into the epidermis.

GB 1 533 119 discloses that niacinamide is useful as a skin lightening agent without causing skin flushing reaction due to vasodialation of blood vessels which is often associated with niacin.

GB 2230186 discloses that addition of a silicone compound to the composition containing a mixture of sunscreen and niacinamide improves the coverage of the cream on the skin for improved protection against the UV light.

The applicants have found that the protection of skin against UV light by compositions containing sunscreens is enhanced when the sunscreen is dissolved in an oil phase. More specifically the applicants have found that the use of the sunscreen dissolved in oil phase has improved sunscreen efficacy than that which may be obtained otherwise by using the sunscreen at substantially higher levels. Thus, the amount of sunscreen required to achieve the same UV protection is reduced by the present invention.

Accordingly the present invention provides a topical cosmetic sunscreen composition comprising from (i) 0.1 to 10% by weight of the composition of an ultra-violet radiation absorbing sunscreen dissolved in an oil; and (ii) a cosmetically acceptable vehicle. The composition is preferably obtained by the process below provided by the present invention.

The present invention also provides a process for the preparation of a cosmetic sunscreen composition comprising the steps of:
(i) dissolving 0.1 to 10% by weight of the composition of an ultra-violet radiation absorbing sunscreen in an oil phase;
(ii) neutralising stearic acid in a water phase; and
(iii) homogenising the dissolved sunscreen with the neutralised stearic acid and a cosmetically acceptable vehicle.

The dissolved sunscreen may be homogenised with the neutralised stearic acid and subsequently blended with the vehicle (and other ingredients) of the composition: It is preferable however for the neutralised stearic acid and vehicle to be blended together and the dissolved sunscreen subsequently to be added to the blend as this has been found to give a composition with an optimal sunscreen effect.

Preferably the stearic acid is neutralised with an alkali such as potassium hydroxide. It is preferred that prior to step (ii) the stearic acid is melted at a temperature above 70° C.

The sunscreen is preferably chosen from 4-tertiary butyl-4'-methoxy dibenzoylemethane, available under the trade name PARSOL 1789 ex Givaudan, 2-ethyl hexyl methoxy cinnamate, available under the trade name PARSOL MCX ex Givaudan or mixtures of the two sunscreen compounds. The composition comprises 0.1 to 10% by weight of the composition and preferably 0.1 to 5% by weight of the composition of a sunscreen compound.

The oil can be mineral oil, vegetable oil or from any other source but is preferably in the liquid state at temperatures greater than 20° C. The oil can be selected from mineral oil, ground nut oil, sunflower oil, safflower oil, til oil or mixtures thereof. But if the preferred process is used where the sunscreens are dissolved in the oil phase and these are subsequently added to the blended neutralised stearic acid and vehicle in the water phase, then the oil need not be one which is in the liquid state at temperatures above 20° C. Suitable oils in these circumstances include isopropyl myristate.

In a one embodiment the stearic acid is first melted at 70° C. and then neutralised with aqueous potassium hydroxide to which sunscreen dissolved in oil is added after the emulsion has cooled to a temperature of less than 50° C. This emulsion forms the base for all other ingredients. All other ingredients may then be homogenised with the base. In a preferred embodiment, these other ingredients are blended with stearic acid/water phase prior to homogenisation with the sunscreen/oil phase.

The composition of the invention-may optionally comprise from 0.1 to 10%, preferably 0.5 to 5% by weight of one or more skin whitening agents. The skin whitening agent is preferably chosen from niacin, niacinamide or a precursor thereof that is capable of releasing niacinamide on the skin. Niacinamide is the amide of niacin and is also known as nicotinamide or pyridine-3-carboxylic acid. An example of a compound which is a niacinamide precursor is niacinamide ascorbate. Other suitable skin whitening agents include extracts of placenta, hydroquinone and derivatives (eg. arbutin), kojic acid, dicarboxylic acids (azelaic acid, sebacic acid), represented by the formula $HOOC-(C_xH_y)-COOH$ where x=4 to 20 and y=6 to 40, ascorbic acid and derivatives thereof, hydroxy acids (lactic acid, glycolic acid, malic acid, tartaric acid etc), ferulic acid, retinol and derivatives or any other known skin whitening compounds.

The vehicle which forms part of the cosmetic composition is one or more substances which are mutually compatible with the sunscreen and if present, the skin whitening agent, and does not harm the skin. The vehicle can act as a diluent, dispersant or carrier for the other ingredients of the composition, and is therefore intended to ensure that they can be readily applied to and distributed evenly over the skin at an appropriate concentration.

The vehicles that can be used in compositions according to the invention can include water, powder absorbents, binders and carriers and liquids such as emollients, propellants, solvents, humectants and thickeners.

Compositions according to the invention can be prepared for topical application to the skin in the form of conventional product types such as creams, lotions, ointments and aerosol products.

The invention is further illustrated by reference to the following examples.

EXAMPLES

Example 1

Process for Preparing the Composition According to the Invention 60 g of water along with 0.48 g of potassium hydroxide was heated to 70° C. in the main mixer. 16 g of stearic acid, 4.4 g Isopropyl palmitate, 0.15 g propyl paraben was heated to 70° C. in the side vessel and was added to the main mixer and mixed well. To this other conventional ingredients, 1 g niacinamide, perfume, water were added and blended well. The mixture was cooled to 30° C. and 0.4 g of Parsol 1789 and 1.2 g of Parsol MCX dissolved in 2 g of mineral oil was homogenised with the rest of the formulation.

Conventional Process 60 g of water and 0.48 g of potassium hydroxide was taken in the main mixer. 16 g of stearic acid, 0.15 g propyl paraben 0.2 g of silicone and 4.4 g of Isopropyl palmitate was blended and heated to 70° C. in a side vessel and in a portion of this mix the 0.4 g of Parsol 1789 and 1.2 g of Parsol MCX was dissolved. Both these mixtures were added into the main mixer under stirring and blended well. Other conventional ingredients, 1 g niacinamide, perfume, water to make to 100 g were added and mixed well by stirring.

Example 2

Spread and Delivery of the Sunscreens on the Skin

The forearms of 15 volunteers were washed with a soap and the surface was dabbed dry and the cream was applied half an hour later to ensure adequate and uniform drying of the forearms. Areas of 2 cm×3 each using a template were marked. 30 mg of cream was applied using a glass rod with adequate care to spread it only inside the markings. Impressions of the experimental regions was taken individually using a cellophane tape from a dispenser with sufficient care not to smudge the surfaces. The tapes were placed on a frame. The different treatments were as follows.

Example 2a

Cream containing no sunscreen or niacinamide (placebo)

Example 2b

Creams prepared by the conventional process described above where in the sunscreens (Parsol 1789 at 0.4% and Parsol MCX were at 1.2% by weight of the composition) and the Niacinamide level was 1.0%.

Example 2c

Creams prepared as in Example 2b but containing double the level of sunscreens (Parsol 1789 at 0.8% and Parsol MCX at 2.4% by weight of the composition) and niacinamide at 2.0%.

Example 2d

Creams prepared according to the invention as described above in which sunscreens (Parsol 1789 at 0.4% and Parsol MCX at 1.2% by weight of the composition) dissolved in mineral oil was added. Niacinamide at 1.0% was added.

Determination of Uniformity of Spread of the Cream

The frame with tapes was placed on a UV source such that the sticky surface of the tape faces downwards. A UV filter was placed over the source to ensure a UV light of constant intensity in the range of 240–350 nm. was obtained. A thin uniform film of a fluorescent dye CBS-X which has an absorption maximum of 368 nm and emission maximum of 406 and 426 nm, as a 2% solution in 1:1 gycerol:water was taken between two cover slips and placed on the non glue side of the tape. This enabled the emission of a visible light wherever there was UV light coming through the tape which was picked up by the video camera with a macroscopic lens (6x) was used.

Thus wherever sunscreen was present UV light would be blocked and the fluorescer would not be excited thus giving a black area. The video camera was connected to a computer with a frame grabber card and using this images were stored. Using the Optimas image analysis software it was possible to quantify the difference in the amount of UV light passing through the tape. The lesser the intensity the better will be the UV blockage and thus better sunscreen efficacy. In addition, to macrophotography and intensity measurement using advanced image analysis techniques, the actual amount of UV A and UV B transmitted was also measured using specific probes for UV A and UV B.

The Table 1 shows that the efficacy of sunscreen in the formulation prepared according to the invention will be superior to creams prepared by the conventional process and is comparable to creams having double the amount of sunscreen in a formulation prepared according the conventional process.

TABLE 1

| Examples | Intensity | UV A | UV B |
| --- | --- | --- | --- |
| 2a | 54.17 | 0.25 | 0.21 |
| 2b | 43.62 | 0.15 | 0.08 |
| 2c | 23.06 | 0.08 | 0.02 |
| 2d | 32.46 | 0.10 | 0.03 |

Example 3

In Vivo Skin Lightening Data

20 Volunteers were selected who applied 0.75 g of the cream prepared according to the invention (2d), or creams prepared according to the conventional process (2b) or the placebo (2a) on one of their forearms twice daily. The other forearm was maintained as unapplied control. The skin tone was evaluated on a 10 point scale one day prior to the application and after 8 weeks of application. The data presented in Table 2 is a change in the score after 8 weeks of application. A negative score indicates a lighter skin tone as compared to the control and a positive score indicates darker skin tone as compared to the control.

TABLE 2

| Example | Score |
|---------|-------|
| 2a | +0.04 |
| 2b | −0.42 |
| 2d | −0.54 |

Example 4

The following creams were fielded in a double blind skin lightening clinical trial. 20 volunteers were selected who applied 0.75 g of creams prepared according to the invention as described in example 1 but using 2% isopropyl myristate (instead of mineral oil) as the oil phase (3a), or creams prepared according to the conventional process (2b), on one of their forearms twice daily. The other forearm was maintained as unapplied control. The skin tone was visually evaluated on a 10 point scale one day prior to application and after 8 weeks of application. The data presented in Table 3 is a change in the score after 8 weeks of application. A negative score indicates a lighter skin tone as compared to the control.

TABLE 3

|    | Trial 1 | Trial 2 |
|----|---------|---------|
| 2b | −0.46   | −0.30   |
| 3a | −0.51   | −0.39   |

What is claimed is:

1. A process for preparing a sunscreen composition comprising the steps of:
    (i) dissolving 0.1 to 10% by weight of the composition of an ultraviolet radiation absorbing sunscreen in an oil phase;
    (ii) neutralising stearic acid in a water phase; and
    (iii) homogenising the dissolved sunscreen with the neutralised stearic acid and a cosmetically acceptable vehicle.

2. A process according to claim 1 wherein the dissolved sunscreen is homogenised with the neutralised stearic acid and cosmetically acceptable vehicle after the neutralised stearic acid and cosmetically acceptable vehicle have been homogenised.

3. A process according to claim 1 comprising the additional step of melting the stearic acid at a temperature above 70° C. prior to step (ii).

4. A process according to claim 1 wherein the oil phase is isopropyl myristate.

5. A topical cosmetic sunscreen composition obtainable by the process according to claim 1.

* * * * *